United States Patent
Kimura et al.

(10) Patent No.: US 11,160,992 B2
(45) Date of Patent: Nov. 2, 2021

(54) LIGHT-EMITTING CAPSULE TREATMENT TOOL

(71) Applicants: PIOLAX, INC., Yokohama (JP); PIOLAX MEDICAL DEVICES, INC., Yokohama (JP); B & PLUS K.K., Hikigun Saitama (JP)

(72) Inventors: Toshihiro Kimura, Yokohama (JP); Satoshi Yoshita, Yokohama (JP); Yasuo Yoshikawa, Yokohama (JP); Takayuki Shindo, Hikigun Saitama (JP)

(73) Assignees: PIOLAX, INC., Yokohama (JP); PIOLAX MEDICAL DEVICES, INC., Yokohama (JP); B & PLUS K.K., Saitama (JP)

(*) Notice: Subject to any disclaimer, the term of this patent is extended or adjusted under 35 U.S.C. 154(b) by 274 days.

(21) Appl. No.: 16/462,517

(22) PCT Filed: Nov. 15, 2017

(86) PCT No.: PCT/JP2017/041108
§ 371 (c)(1),
(2) Date: May 20, 2019

(87) PCT Pub. No.: WO2018/097005
PCT Pub. Date: May 31, 2018

(65) Prior Publication Data
US 2019/0344093 A1   Nov. 14, 2019

(30) Foreign Application Priority Data
Nov. 22, 2016  (JP) .............................. JP2016-227180

(51) Int. Cl.
*A61N 5/06* (2006.01)
*F21V 23/02* (2006.01)
(Continued)

(52) U.S. Cl.
CPC ........... *A61N 5/0603* (2013.01); *A61N 5/062* (2013.01); *F21V 23/02* (2013.01);
(Continued)

(58) Field of Classification Search
CPC .......... A61N 5/0603; A61N 2005/0651; A61N 1/37211; A61N 1/37217; A61N 1/37223;
(Continued)

(56) References Cited

U.S. PATENT DOCUMENTS

| | | | |
|---|---|---|---|
| 2005/0154294 A1* | 7/2005 | Uchiyama | A61B 1/0676 600/420 |
| 2009/0018396 A1* | 1/2009 | Takizawa | A61B 5/07 600/127 |

(Continued)

FOREIGN PATENT DOCUMENTS

| | | |
|---|---|---|
| JP | 2002-000556 A | 1/2002 |
| JP | 2005-006753 A | 1/2005 |

(Continued)

OTHER PUBLICATIONS

Mitsunaga, Makoto, et al., Cancer; cell-selective in vivo near infrared photoimmunotherapy targeting specific membrane molecules, Nature Medicine, Nov. 6, 2011, vol. 17, No. 12, pp. 1685-1691.

(Continued)

*Primary Examiner* — Allen Porter
*Assistant Examiner* — James Moss
(74) *Attorney, Agent, or Firm* — McGinn I.P. Law Group, PLLC

(57) ABSTRACT

A light emitting type capsule treatment tool for irradiating light with a specific wavelength required for photoimmunotherapy, includes a power receiving coil, a magnetic member, a light emitting member and a capsule. The power receiving coil is formed by winding a conductive wire and (Continued)

configured to receive electric power supplied from an external transmission antenna via a magnetic flux. The magnetic member is placed on an inner circumference of the power receiving coil. The light emitting member is configured to be supplied with electric power from the power receiving coil and to emit the light with the specific wavelength. The capsule houses the power receiving coil, the magnetic member and the light emitting member.

3 Claims, 15 Drawing Sheets

(51) Int. Cl.
A61B 17/00 (2006.01)
F21W 131/20 (2006.01)
(52) U.S. Cl.
CPC ........... A61B 2017/00283 (2013.01); A61B 2017/00876 (2013.01); A61B 2560/0219 (2013.01); A61N 2005/0609 (2013.01); A61N 2005/0612 (2013.01); A61N 2005/0651 (2013.01); A61N 2005/0659 (2013.01); A61N 2005/0668 (2013.01); F21W 2131/20 (2013.01)
(58) Field of Classification Search
CPC ........... A61N 1/37229; A61N 1/3787; A61N 1/3756; A61N 1/37518; A61B 2017/00283; A61B 2560/0219
USPC .......................................................... 607/92
See application file for complete search history.

(56) References Cited

U.S. PATENT DOCUMENTS

2013/0172672 A1* 7/2013 Iddan .................. A61B 1/041
                                                           600/109
2014/0378760 A1* 12/2014 Ito ..................... H02K 33/14
                                                           600/103

FOREIGN PATENT DOCUMENTS

| JP | 2006-055287 A |   | 3/2006  |              |
|----|---------------|---|---------|--------------|
| JP | 2007-020951 A |   | 2/2007  |              |
| JP | 2007020951 A  | * | 2/2007  | ... A61B 5/07 |
| JP | 2013-230211 A |   | 11/2013 |              |
| JP | 2016-127700 A |   | 7/2016  |              |
| JP | 2016127700 A  | * | 7/2016  |              |

OTHER PUBLICATIONS

International Search Report (ISR) (PCT Form PCT/ISA/210), in PCT/JP2017/041108, dated Jan. 9, 2018, and English Translation thereof.
Written Opinion of the International Searching Authority (PCT/ISA/237), in PCT/JP2017/041108, dated Jan. 9, 2018.
(PCT/IPEA/408), in PCT/JP2017/041108, dated Jul. 24, 2018.
(PCT/IPEA/409), in PCT/JP2017/041108 (English version) International Preliminary Report on Patentability (PCT/IPEA/409), in PCT/JP2017/041108, dated Nov. 20, 2018, and English Translation thereof.

* cited by examiner (a)

(b)

LIGHT-EMITTING CAPSULE TREATMENT TOOL

TECHNICAL FIELD

The present invention relates to light emitting type capsule treatment tools for irradiating light with a specific wavelength required for photoimmunotherapy.

BACKGROUND ART

In recent years, as cancer therapy, photoimmunotherapy has attracted attention, which is a method by which tumor cells are selectively destroyed without damaging normal tissue. A mechanism of cancer therapy using this photoimmunotherapy is as follows.

In general, immune cells (killer t cells) that destroy cancer cells exist around cancer cells; however, immune suppressor cells surrounding the cancer cells suppress the action of the killer t cells. Thus, monoclonal antibodies (MAb) that recognize specific protein on the surfaces of cancer cells or immune suppressor cells around the cancer cells are conjugated with photosensitive substances having the function of absorbing light with a specific wavelength (e.g., near-infrared light) to bring about a chemical reaction to generate heat to destroy the cells, and then the monoclonal antibodies with which the photosensitive substances are conjugated are given into a body, whereby the photosensitive substances are specifically attached to the surfaces of the cancer cells or immune suppressor cells around the cancer cells via the monoclonal antibodies, and in this state, light with a wavelength to which the photosensitive substances react is irradiated to bring about a chemical reaction to the photosensitive substances, and thus the cancer cells and the immune suppressor cells to which the photosensitive substances are attached are destroyed. For example, IR700 (phthalocyanine) absorbing near-infrared light to generate heat is used as the photosensitive substances.

For example, Patent Document 1 described below discloses, as a photo irradiation device used for the above-described treatment, a medical device including photo irradiation means that irradiates light with the wavelength of 810 nm in photodynamic therapy/photodynamic hyperthermal therapy/photodynamic thermochemotherapy. The embodiment of Patent Document 1 describes that a photo irradiation portion including six LEDs and irradiating near-infrared light with the wavelength of 810 nm from the outside of a body is provided.

CITATION LIST

Patent Literature

Patent Document 1: JP-A-2013-230211

SUMMARY OF INVENTION

Technical Problem

As described in the above-described Patent Document 1, when near-infrared light with a specific wavelength is irradiated from the outside of a body, a treatment can be performed even with the near-infrared light irradiated from the outside in some cases because the light has a certain amount of permeability to tissue of a human body. However, there arises a problem in that the light does not effectively reach some affected areas covered with tissue such as thick fat under a skin, and thus the effect of the treatment cannot be enhanced.

An object of the present invention is to provide a light emitting type capsule treatment tool capable of irradiating light with a specific wavelength on an affected area such as cancer tissue from a closer position.

Solution to Problem

In order to achieve the above-described object, a light emitting type capsule treatment tool according to the present invention is for irradiating light with a specific wavelength required for photoimmunotherapy, and includes a power receiving coil formed by winding a conductive wire and configured to receive electric power supplied from an external transmission antenna via a magnetic flux, a magnetic member placed on an inner circumference of the power receiving coil, a light emitting member configured to be supplied with electric power from the power receiving coil and to emit the light with the specific wavelength, and a capsule housing the power receiving coil, the magnetic member and the light emitting member.

Advantageous Effects of Invention

According to the present invention, since the treatment tool has a relatively simple configuration including the power receiving coil, the magnetic member, the light emitting member, and the capsule configured to house these components, the treatment tool can have the shape of a small capsule. Thus, the treatment tool can be easily placed at a point requiring treatment in a body, for example, via an endoscope, a medical tube, or a needle of a biopsy needle, or by being swallowed from a mouth.

By passing an alternating current through the external transmission antenna, and supplying the power receiving coil with the electric power using electromagnetic induction, the light emitting member can emit light with a specific wavelength required for photoimmunotherapy with the electric power supplied from the power receiving coil. Thus, light can be irradiated on a point requiring treatment such as cancer tissue from a closer position, whereby the treatment tool can be preferably used for photoimmunotherapy.

BRIEF DESCRIPTION OF DRAWINGS

FIG. 13(a) is an explanatory view of the treatment tool in a first usage state, and FIG. 13(b) is an explanatory view of the treatment tool in a second usage state.

DESCRIPTION OF EMBODIMENTS

Hereinafter, a description of the light emitting type capsule treatment tool according to the present invention in the first embodiment will be provided with reference to FIGS. 1 to 8.

Figure 1:
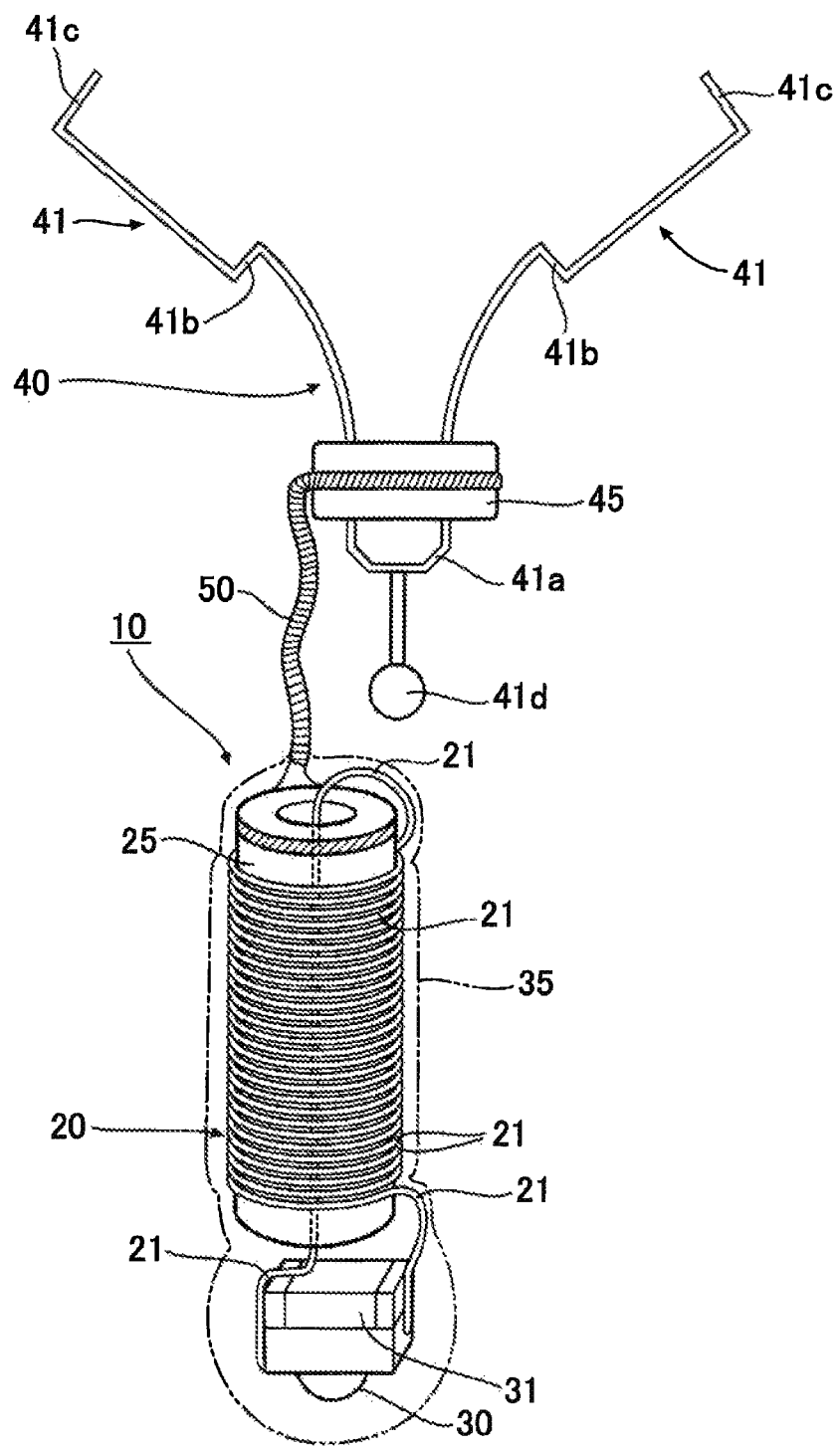
FIG. 1 is a perspective view of a light emitting type capsule treatment tool according to the present invention in the first embodiment.
Figure 2:
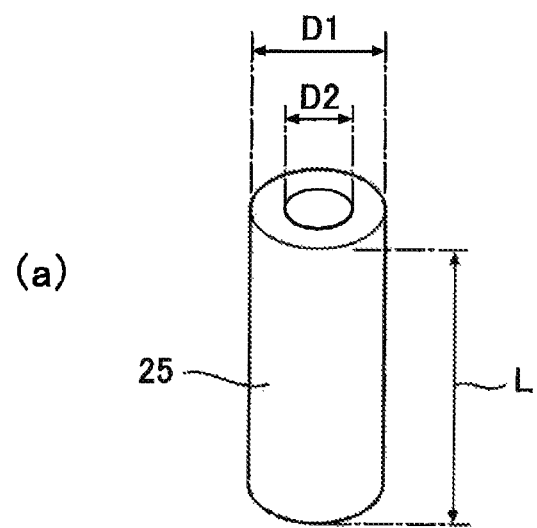
FIG. 2(a) is a perspective view of a magnetic member constituting the treatment tool.
FIG. 2(b) is an explanatory view schematically showing a schematic configuration of the treatment tool.
Figure 2:
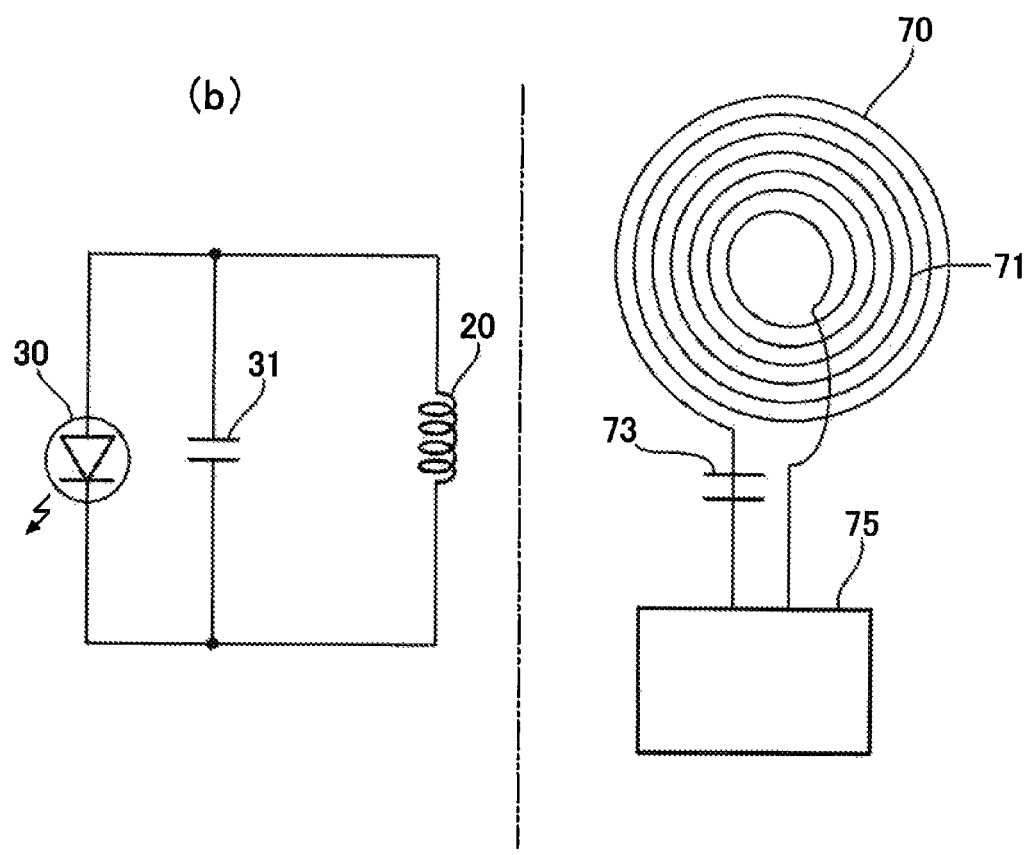

The light emitting type capsule treatment tool is for irradiating light with a specific wavelength required for photoimmunotherapy. As shown in FIG. 1, a light emitting type capsule treatment tool 10 in the present embodiment (hereinafter, referred to simply as the "treatment tool 10") includes a power receiving coil 20 formed by winding a conductive wire 21 and configured to receive electric power supplied from an external transmission antenna 70 (see FIG. 2) via a magnetic flux, a magnetic member 25 placed on an inner circumference of the power receiving coil 20, a light emitting member 30 configured to be supplied with electric power from the power receiving coil 20 to emit light with a specific wavelength, and a capsule 35 housing these components.

As shown in FIG. 1, the power receiving coil 20 in the present embodiment is formed by winding (helical winding) the conductive wire 21 so as to have a circular cylinder shape. The magnetic member 25 placed on the inner circumference of the power receiving coil 20 also has a circular cylinder shape (see FIG. 2(a)).

In addition, as shown in FIG. 1, the conductive wire 21 making up the power receiving coil 20 is wound from one end side in the axial direction of the magnetic member 25 (the lower end side in FIG. 1) to the other end side in the axial direction, and one end of the conductive wire 21 is drawn to the one end side in the axial direction of the magnetic member 25 through the interior space of the magnetic member 25 while the other end is drawn from the outer circumference on the other end side in the axial direction of the magnetic member 25.

It is to be noted that in the embodiment shown in FIG. 1, the conductive wire 21 is formed with a given pitch; however, the conductive wire 21 may be densely wound or may be wound in multi-layers, and the winding manner is not particularly limited. In addition, the conductive wire 21 has a wire diameter that is preferably 0.05 to 0.15 mm and more preferably 0.08 to 0.12 mm. In addition, the power receiving coil 20 has an outer diameter that is preferably 2.5 mm or less and more preferably 2.0 mm or less. Further, the power receiving coil 20 has an axial length that is preferably 1 to 5 mm and more preferably 2 to 3 mm.

In addition, as shown in FIG. 2(a), the magnetic member 25 of a circular cylinder shape has a length L that is preferably 3 to 6 mm and more preferably 4 to 5 mm. Further, the magnetic member 25 has an outer diameter D1 that is preferably 2 mm or less and more preferably 1.8 mm or less, and has an inner diameter D2 that is preferably 1 mm or less and more preferably 0.5 mm or less.

It is to be noted that while the magnetic member 25 in the present embodiment has a circular cylinder shape, the magnetic member 25 may have not only a circular cylinder shape but also may have an angular cylinder shape, or a solid circular column shape/angular column shape, and the shape is not particularly limited. However, it is preferable that the magnetic member 25 should have a cylinder shape if the wound conductive wire 21 is drawn from the one end side in the axial direction of the magnetic member 25 to the other end side in the axial direction as shown in FIG. 1. In addition, the magnetic member 25 can be made from a ferromagnetic material such as ferrite, Fe, iron oxide, Cr oxide, Ni, amorphous, and a permalloy.

In addition, as shown in FIG. 1, the light emitting member 30 is placed on one end side in the axial direction of the power receiving coil 20 concentrically with respect to the shaft center of the power receiving coil 20 via a resonance capacitor 31, and the both ends in the axial direction of the conductive wire 21 are connected to them. It is to be noted that the light emitting member 30 in the present embodiment defines a light-emitting diode (LED). That is, as shown in FIG. 2(b), the power receiving coil 20, the resonance capacitor 31, and the light emitting member 30 are arranged in parallel, and the power receiving coil 20 is connected to the light emitting member 30 defining the light-emitting diode via the resonance capacitor 31 arranged in parallel thereto.

It is to be noted that as the wavelength of the light emitted by the light emitting member 30, a wavelength of light that photosensitive substances to be conjugated with monoclonal antibodies can absorb to bring about a chemical reaction is selected. For example, when IR700 (phthalocyanine) is used as the photosensitive substances, near-infrared light with the wavelengths of 680 to 710 nm is used.

The above-described power receiving coil 20, the magnetic member 25, the resonance capacitor 31, and the light emitting member 30 are housed in the capsule 35, which allows the treatment tool 10 to be inserted or indwelled in a body. The capsule 35 in the present embodiment is a resin molded product having an approximately capsule shape that is formed by coating the outer circumference of the power receiving coil 20, the magnetic member 25, the resonance capacitor 31, and the light emitting member 30 with a permeable resin material, and an end portion of the capsule 35 on the side of the light emitting member 30 has a rounded spherical shape. It is to be noted that a string-shaped member 50 to be described later is drawn from the other end side of the capsule 35.

As described above, a "capsule" in the present invention includes a resin molded product of a capsule shape. However, examples of the capsule include a capsule-shaped product including a pair of containers of a cylinder shape having a spherical end portion, and a capsule-shaped product including a bottomed container of a cylinder shape and a lid body for covering the container, and the capsule is not particularly limited only if the product can house the power receiving coil 20, the magnetic member 25, the resonance capacitor 31, and the like so as to cover them not to expose them to the outside of the capsule.

In addition, the capsule 35 has an outer diameter that is preferably 3.0 mm or less and more preferably 0.5 to 2.0 mm. Further, the capsule 35 has an axial length that is preferably 15 mm or less and more preferably 3 mm or less. In addition, the capsule 35 can be made from, for example, an epoxy resin, polycarbonate, an acrylate resin, or an ABS resin, and it is preferable to use a permeable material for the part that houses the light emitting member 30 in order not to decrease the intensity of light emitted from the light emitting member 30. It is to be noted that the capsule 35 is not illustrated in FIG. 4 or FIG. 6 for the sake of illustration.

In addition, the treatment tool 10 in the present embodiment has a configuration such that the light emitting member 30 is connected concentrically to the one end side in the axial direction of the power receiving coil 20; however, the configuration is not limited thereto. For example, a light emitting type capsule treatment tool 10A (hereinafter, referred to as the "treatment tool 10A") may be used, which has a configuration such that the light emitting members 30 are connected concentrically to both end sides in the axial direction of the power receiving coil 20 via the resonance capacitors 31 as shown in FIG. 7(a). Further, a light emitting type capsule treatment tool 10B (hereinafter, referred to as the "treatment tool 10B") may be used, which has a configuration such that the light emitting members 30 and the resonance capacitors 31 are placed at some midpoint in the axial direction (here, in the middle in the axial direction) of the power receiving coil 20, and connected to both end sides in the axial direction of the power receiving coil 20 via the conductive wires 32 as shown in FIG. 7(b).

It is to be noted that FIG. 7(c) is a circuit diagram of the treatment tools 10A, 10B shown in FIG. 7(a), 7(b). As shown in FIG. 7(c), in each of the treatment tools 10A, 10B, one light emitting member 30 is oriented oppositely to the other light emitting member 30, and the light emitting members 30 are connected in parallel to the resonance capacitor 31 and the power receiving coil 20. Thus, when an alternating current is supplied to the power receiving coil 20 of each of the treatment tools 10A, 10B via the transmission antenna 70 to be described later, the two light emitting members 30, 30 emit light alternately, whereby the alternating current can be used efficiently.

Electric power is supplied from the external transmission antenna 70 to the light emitting member 30 of the treatment tool 10 having the above-described configuration. As shown in FIG. 2(b), the transmission antenna 70 in the present embodiment is made of a conductive wire 71 wound into a planar spiral shape. Here, the conductive wire 71 is planarly wound into a spiral shape at predetermined intervals (spiral winding), and has an annular shape having a void in its center.

In addition, the resonance capacitor 73 and the inverter circuit 75 are connected to the transmission antenna 70. When electric power supplied from an unillustrated electrical power source is converted into an alternating current via the inverter circuit 75, and the alternating current is supplied to the transmission antenna 70 via the resonance capacitor 73, the transmission antenna 70 generates a magnetic field, and its magnetic flux is electromagnetically induced to the power receiving coil 20 of the treatment tool 10, whereby wireless power supply can be carried out (see FIG. 6).

It is to be noted that the transmission antenna 70 has an outer diameter that is preferably 500 mm or less and more preferably 200 mm or less.

Figure 5:
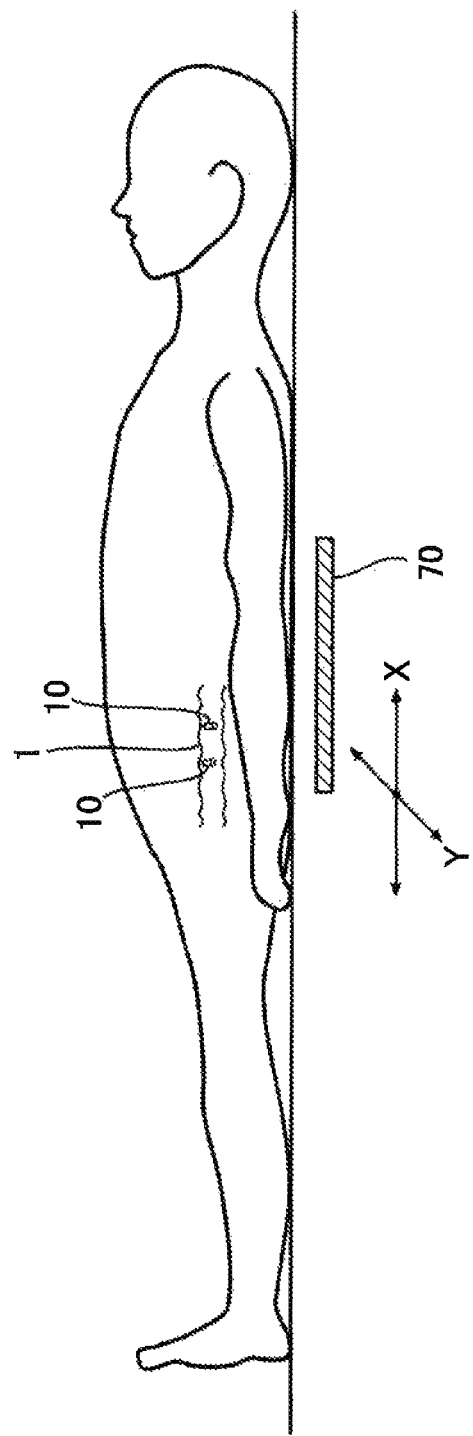
FIG. 5 is an explanatory view of the treatment tool in the case of being applied to a treatment subject.

As shown in FIG. 5, the transmission antenna 70 in the present embodiment is placed under a treatment subject, and can be shifted in the X-axis direction and the Y-axis direction with the use of unillustrated shifting means (a manipulator, etc.).

Further, the treatment tool 10 includes a retaining portion configured to retain the capsule 35 at an intended point in a body.

Figure 3:
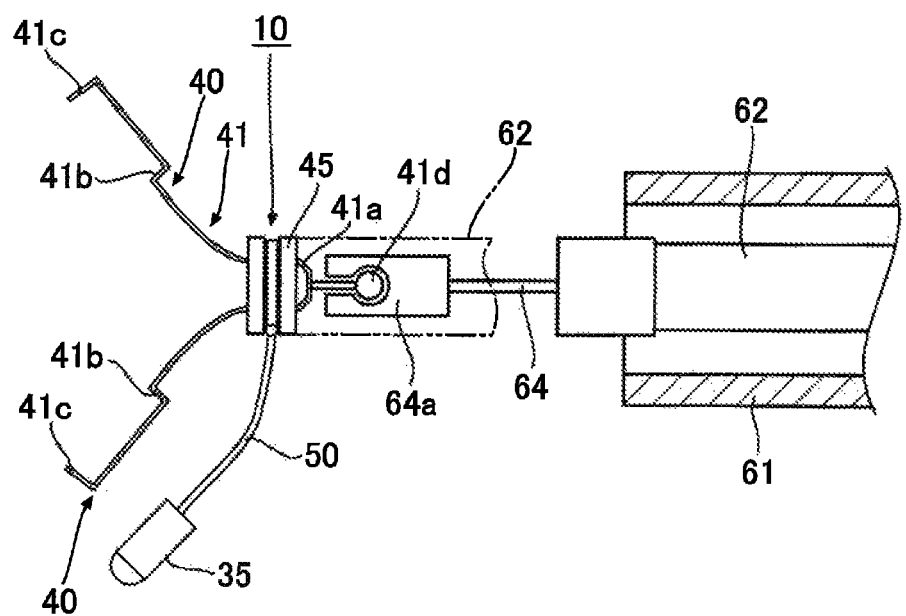
FIG. 3 is an explanatory enlarged view of relevant components of the treatment tool.
Figure 4:
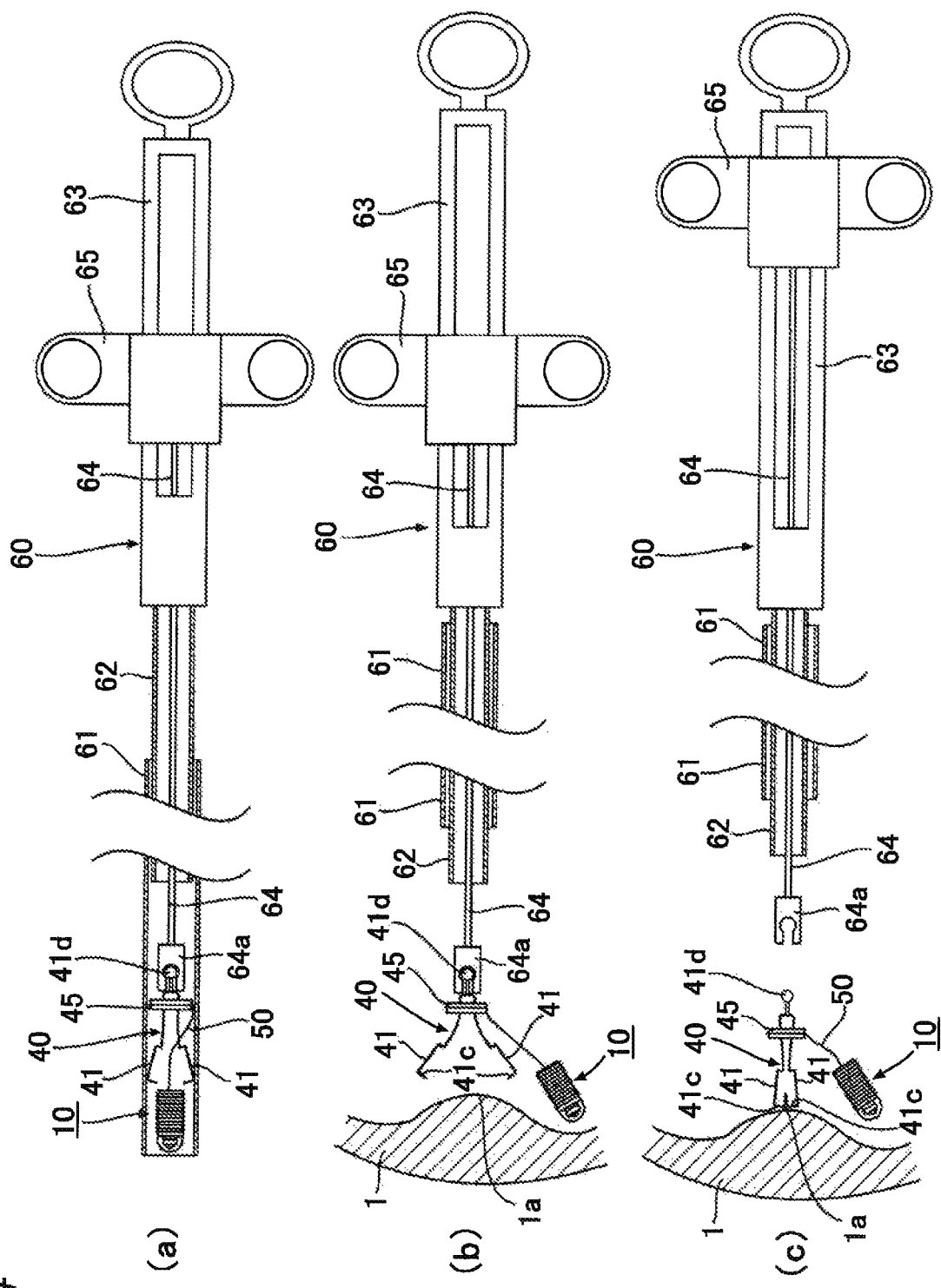
FIG. 4(a) is an explanatory view of the treatment tool in the state of being housed in a distal end portion of a carrier device.
FIG. 4(b) is an explanatory view of the treatment tool in the state of being released out of the distal end portion of the carrier device.
FIG. 4(c) is an explanatory view of the treatment tool in the state of being retained on a wall portion in a body.

As shown in FIG. 1, FIG. 3, and FIG. 4, the retaining portion in the present embodiment defines a clip 40 capable of holding a wall portion in a body. The clip 40 includes a pair of holding pieces 41, 41 configured to be opened and closed and normally urged in a direction to be opened, and a slider 45 attached on an outer circumference of the holding pieces 41, 41 so as to be slid thereon and configured to close the holding pieces 41, 41 by being slid to distal end sides of the holding pieces 41.

To be more specific, the pair of holding pieces 41, 41 have their base end sides coupled with each other via a coupling portion 41a, and their distal end sides urged to get expanded so as to be away from each other into an approximately chevron shape. Each holding piece 41 has such a shape bending outward via a step portion 41b at a midpoint in its length direction while each holding piece 41 has a distal end 41c having a pawl shape bending inward. Further, the coupling portion 41a includes a connecting portion 41d attached to/detached from a carrier device 60 to be described later (see FIG. 4).

Meanwhile, the slider 45 has a circular ring shape, and is placed on the outer circumference on the base end sides of the pair of holding pieces 41, 41. The slider 45 closes, when slid to the distal end sides of the holding pieces 41, the pair of holding pieces 41, 41, and thus can hold some tissue in a body (e.g., an intended point 1a in a wall portion 1 of a tubular organ such as a large intestine) with the pawl-shaped distal ends 41c, 41c (see FIG. 4(c)).

It is to be noted that the shape of the clip is not limited to the above-described shape. For example, the clip may have a shape of further including another holding piece between a pair of holding pieces only if the holding pieces are closed by sliding the slider 45 and can hold some tissue in a body.

In addition, as shown in FIG. 1 and FIG. 3, the clip 40 defining the retaining portion is coupled to the capsule 35 via the string-shaped member 50. In the present embodiment, it is configured that the clip 40 is coupled to the capsule 35 via the string-shaped member 50 on the other end side in the axial direct of the power receiving coil 20, that is, on the opposite side where the light emitting member 30 and the resonance capacitor 31 are. The string-shaped member 50 has its one end coupled to the other end side in the axial direction of the magnetic member 25 and the other end coupled to the slider 45 of the clip 40. In addition, the string-shaped member 50 in the present embodiment defines a strand made of stranded wires.

The above-described string-shaped member 50 can be made of wire materials made of synthetic resins such as polypropylene, a nylon elastomer, polyether block amide, polyethylene, polylactic acid, polyester, and polyether ether ketone, or metal wire materials made of Ni—Ti, stainless steel, gold, titanium, tantalum, platinum, and iridium, and alloys thereof. Among them, polyester, a nylon elastomer, and polypropylene are preferably used as having biocompatibility.

In addition, the string-shaped member 50 has a length that is preferably 15 mm or less and more preferably 10 mm or less.

Figure 8:
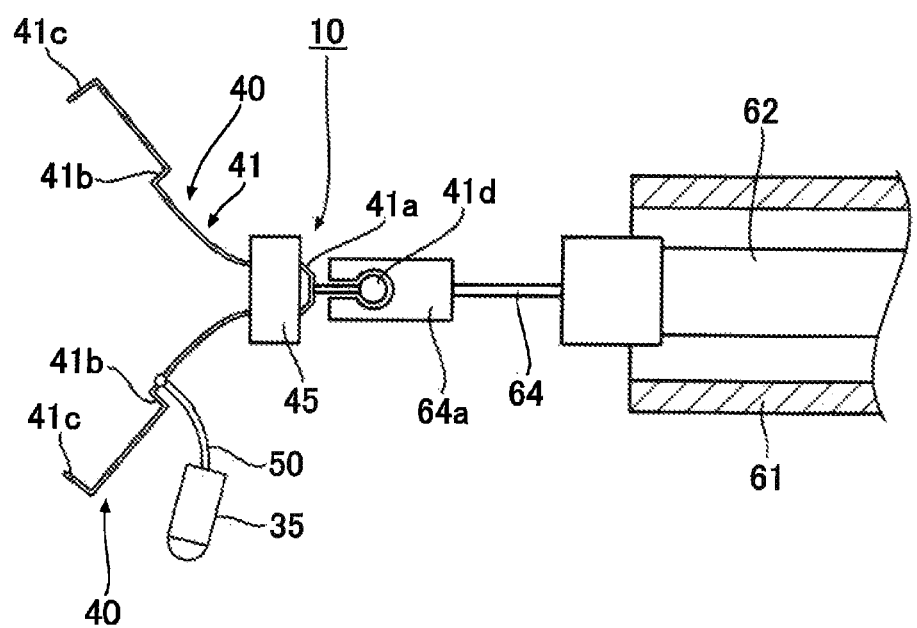
FIG. 8 is an explanatory view of the treatment tool showing a variant of the coupling point of the clip.

It is to be noted that while the other end of the string-shaped member 50 is coupled to the slider 45 of the clip 40 in the present embodiment, the other end of the string-shaped member 50 may be coupled to the holding piece 41 constituting the clip 40 at a portion at some midpoint in the axial direction close to the step portion 41b as shown in FIG. 8, and the portion to be coupled to is not particularly limited.

Next, a description of the carrier device 60 that carries the treatment tool 10 having the above-described configuration to a predetermined point in a body will be provided with reference to FIG. 4. The carrier device 60 includes an outer sheath 61 having a tubular shape, an inner sheath 62 having a tubular shape and inserted to be placed in the outer sheath 61 in a slidable manner, and a sheath holding portion 63 attached to the inner sheath 62 on the base end side. A manipulation wire 64 is placed in the inner sheath 62 in a slidable manner, and a chuck portion 64a that makes the connecting portion 41d of the clip 40 attachable thereto/detachable therefrom is provided at the distal end of the manipulation wire 64. In addition, a wire manipulating portion 65 is placed on the outer circumference of the sheath holding portion 63 in a slidable manner, and is coupled to the manipulation wire 64 on the base end side.

For example, when the outer sheath 61 is slid back and forth in the sheath axial direction while the sheath holding portion 63 is held, the outer sheath 61 is slid with respect to the inner sheath 62, and when the wire manipulating portion 65 is slid back and forth in the sheath axial direction while the sheath holding portion 63 is held, the manipulation wire 64 is slid with respect to the inner sheath 62. It is to be noted that the sheath holding portion 63 may be slid while the inner sheath 62 is held, or the sheath holding portion 63 may be slid while the wire manipulating portion 65 is held, and the manipulation method is not particularly limited. In addition, the carrier device is not limited to ones having the above-described configuration, and any carrier devices capable of carrying the treatment tool 10 may be used.

Next, one example of a method for using the treatment tool 10 according to the present invention having the above-described configuration will be provided. It is to be noted that the using method is merely one example, and is not particularly limited.

Figure 6:
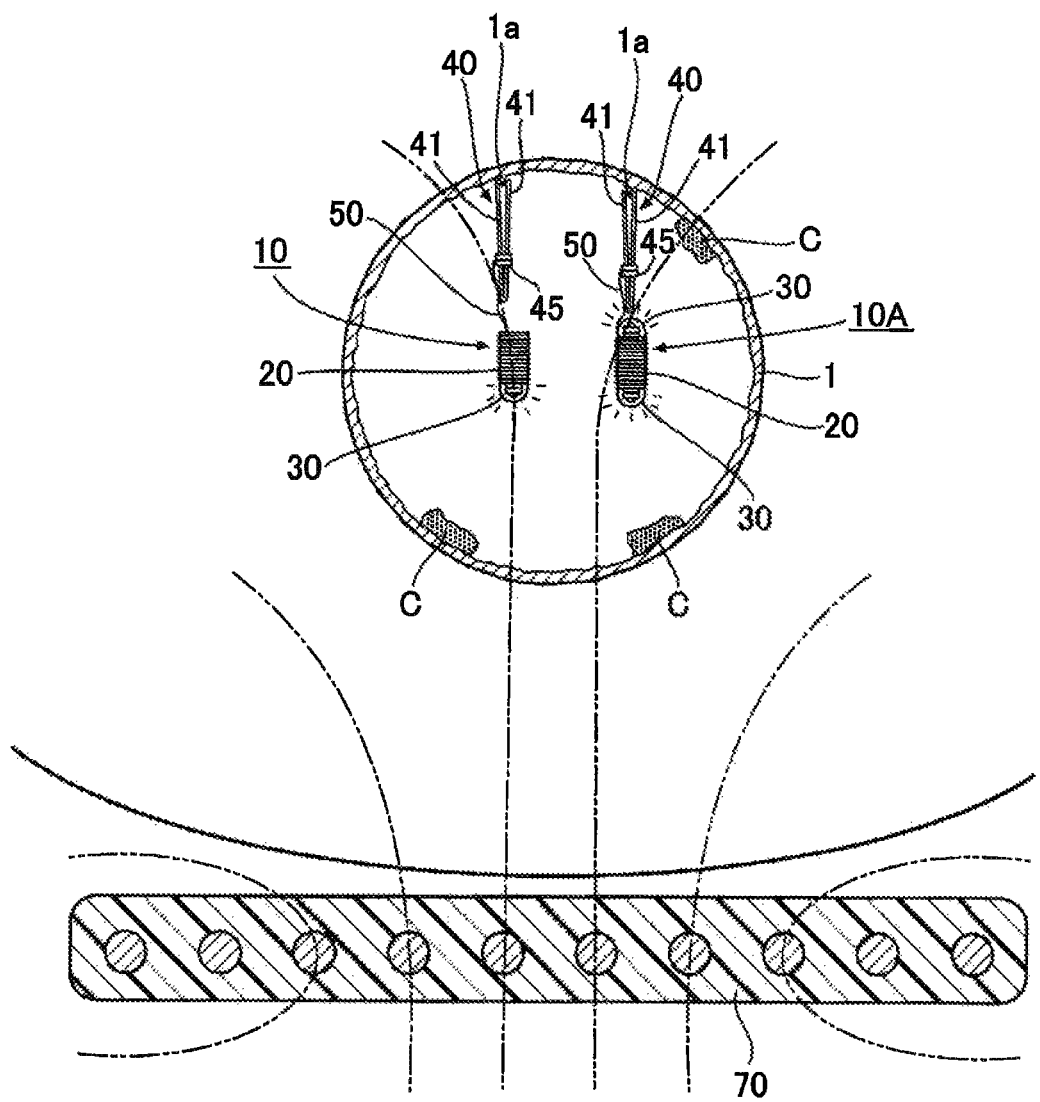
FIG. 6 is an explanatory view of the treatment tool in the state of being indwelled on the wall portion in the body.
Figure 7:
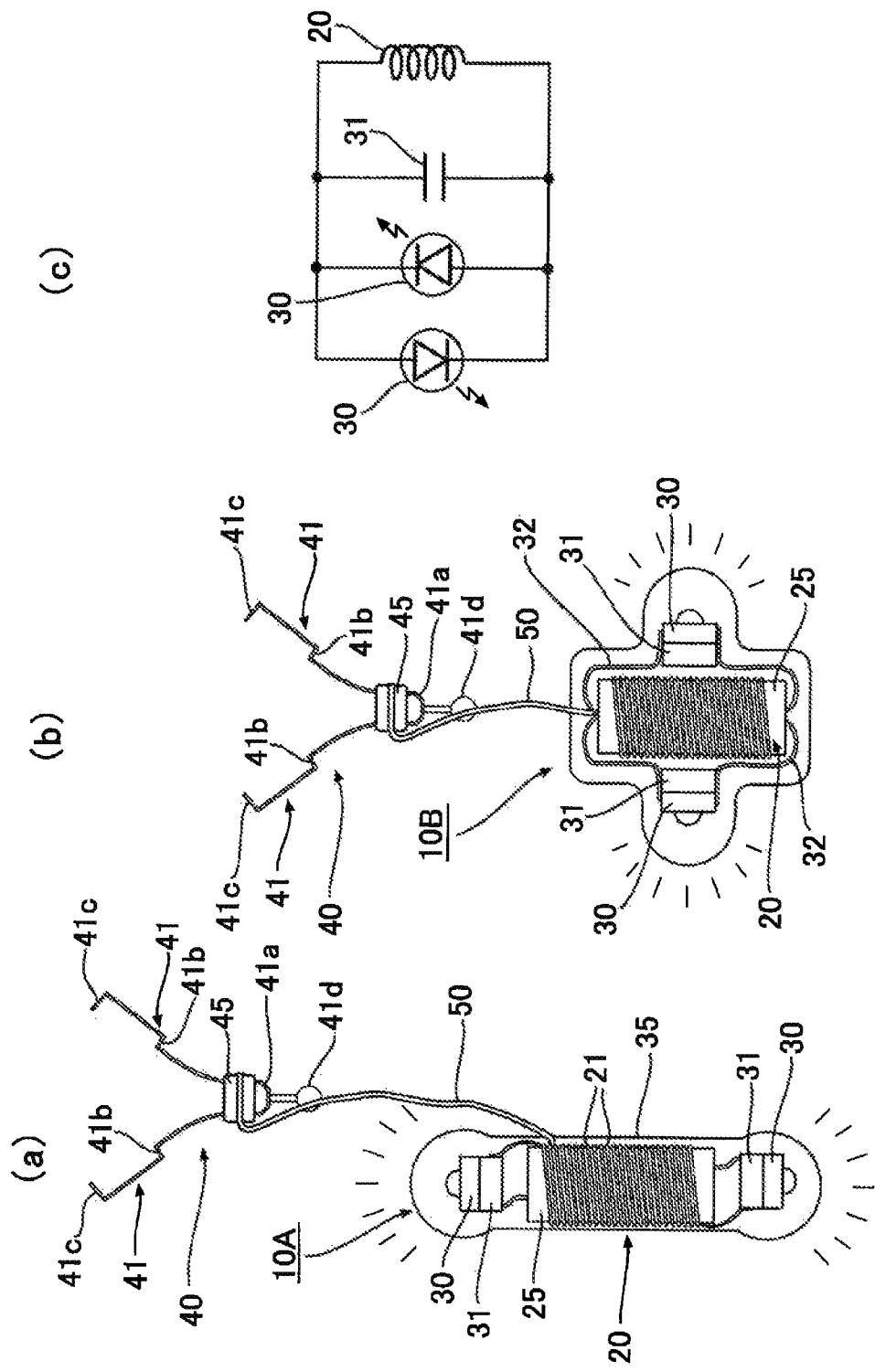
FIG. 7(a) is an explanatory view of a first variant of the treatment tool.
FIG. 7(b) is an explanatory view of a second variant of the treatment tool.
FIG. 7(c) is a circuit diagram of the variants shown in FIGS. 7(a) and 7(b).

As shown in FIG. 6, in the present embodiment, the treatment tool 10 is retained at a predetermined point 1a in the wall portion 1 in a body via the clip 40 that defines the retaining portion, whereby light is irradiated on affected areas C (for example, cancer cells) generated in the wall portion 1. The inside of a body in the present embodiment specifically defines a large intestine; however, the inside of a body may be an organ such as a stomach as well as a large intestine, and further may be tubular organs such as an intestine duodenum, a biliary duct, and a pancreatic duct, and is not particularly limited.

First, in the clip 40, the slider 45 is placed on the outer circumference on the base end side of the holding pieces 41, and the pair of holding pieces 41, 41 is made expanded as shown in FIG. 1 and FIG. 3.

In addition, while the sheath holding portion 63 of the carrier device 60 is held, the outer sheath 61 is slid to the opposite side to the hand side of a manipulator (hereinafter, referred to simply as the "sheath's distal end side"), and the distal end portion of the outer sheath 61 is projected further than the distal end portion of the inner sheath 62. Further, while the sheath holding portion 63 is held, the wire manipulating portion 65 is slid to the sheath's distal end side, and the manipulation wire 64 is pushed out to make the chuck portion 64a exit from the tip opening of the outer sheath 61.

Then, as shown in FIG. 3, the connecting portion 41d of the clip 40 is connected to the chuck portion 64a of the manipulation wire 64. In this state, while the sheath holding portion 63 of the carrier device 60 is held, the wire manipulating portion 65 is pulled to the hand side of the manipulator. Then, the manipulation wire 64 is pulled to pull the clip 40 via the chuck portion 64a, and thus the pair of expanded holding pieces 41, 41 is sucked into the outer sheath 61 to be pressed by the inner circumferential surface thereof, and as a result, the pair of holding pieces 41, 41 is closed against the elastic force, and thus as shown in FIG. 4(a), the treatment tool 10 is housed in the inner circumference of the distal end portion of the outer sheath 61.

Then, as shown in FIG. 5, an unillustrated endoscope is inserted from the mouth of a treatment subject lying on his/her back, the distal end portion of the endoscope is shifted to a predetermined position in his/her body, then the entire carrier device 60 housing the treatment tool 10 is kept shifted through the lumen of the endoscope, and the distal end portion is shifted to a position a little short of an intended position in the wall portion 1 in the body. Then, while the sheath holding portion 63 of the carrier device 60 is held, the outer sheath 61 is slid to the hand side of the manipulator (see the arrow in FIG. 4(a)). This releases the treatment tool 10 from the tip opening of the outer sheath 61, and the pair of holding pieces 41, 41 of the clip 40 is expanded as shown in FIG. 4(b). Then, the distal ends 41c, 41c of the pair of expanded holding pieces 41, 41 are brought into contact with the intended point 1a in the wall portion 1, and while the wire manipulating portion 65 is held in this state, the inner sheath 62 is pushed out to the distal end side via the sheath holding portion 63.

Then, the slider 45 of the clip 40 is pushed to the holding pieces' distal end sides by the distal end of the inner sheath 62, and the pair of holding pieces 41, 41 is closed to be kept in this state, and thus the intended point 1a in the wall portion 1 in the body can be pinched by the distal ends 41c, 41c of the pair of holding pieces 41, 41 as shown in FIG. 4(c). Then, the inner sheath 62 is pressed against the slider 45 (see the imaginary line in FIG. 3) to regulate the movement of the slider 45 to pull the wire manipulating portion 65 to the hand side, whereby the connection between the chuck portion 64a and the connecting portion 41d of the clip 40 is released (see FIG. 4(c)), whereby the carrier device 60 can be pulled out of the body while only the treatment tool 10 and the treatment tool 10A are left in the body as shown in FIG. 6.

As described above, the treatment tool 10 and the treatment tool 10A can be retained at the intended points 1a in the wall portion 1 in the body via the clips 40 as shown in FIG. 6. Then, the transmission antenna 70 is installed under the treatment subject as shown in FIG. 5 to supply the transmission antenna 70 with electric power from an unillustrated electrical power source. Then, an alternating current converted via the inverter circuit 75 is supplied to the conductive wire 71 of the transmission antenna 70 via the resonance capacitor 73 to generate a magnetic field, and a magnetic flux thereof is electromagnetically induced to the power receiving coil 20 of the treatment tool 10, whereby wireless power supply can be carried out as shown in FIG.

6. Then, the alternating current that the power receiving coil 20 has received is supplied to the light emitting member 30, whereby light with a predetermined wavelength can be emitted.

At this time, while light with a specific wavelength has been conventionally irradiated only from the outside of a body in irradiating the light with a specific wavelength in photoimmunotherapy, the treatment tools 10, 10A can irradiate the light with a specific wavelength on an affected area C generated in the wall portion 1 in the body from a closer position as shown in FIG. 6, and thus the treatment tools 10, 10A can be preferably used in photoimmunotherapy.

In addition, since the treatment tools 10, 10A have a relatively simple configuration including the power receiving coil 20, the magnetic member 25, the light emitting member 30, and the capsule 35 housing these components, the treatment tools 10, 10A can have the shape of a small capsule. Thus, as described above, the treatment tools 10, 10A can be easily placed at a point requiring treatment in a body, for example, via an unillustrated endoscope, the medical tube 95 to be described later (see FIG. 14), or a needle of a biopsy needle 91 (see FIG. 13), or further by being swallowed from a mouth (see FIG. 15).

Further in the present embodiment, the retaining portion (here, the clip 40) configured to retain the capsule 35 at an intended point in a body is further included. Thus, the capsule 35 can be indwelled at the intended point 1a in the wall portion 1 in the body as shown in FIG. 6, whereby light can be irradiated on the affected area C requiring treatment from a closer position in an effective manner for required time.

In addition, in the present embodiment, the retaining portion includes the clip 40 including the pair of holding pieces 41, 41 openable and closable and normally urged in the opening direction, and the slider 45 attached in a slidable manner on the outer circumference of the holding pieces 41, 41 and capable of closing the holding pieces 41, 41 by being slid to the distal end sides of the holding pieces 41. Thus, by bringing, while the pair of holding pieces 41, 41 is expanded, the distal end portions thereof into contact with the intended point 1a in the wall portion 1 in the body and sliding the slider 45 to the distal end side, the pair of holding pieces 41, 41 is closed to be allowed to pinch the intended point 1a in the wall portion 1 in the body. In this manner, the capsule 35 can be easily retained on the wall portion 1 in the body via the clip 40, and the operation to indwell the treatment tools 10, 10A can be carried out with ease.

Further in the present embodiment, since the clip 40 defining the retaining portion is coupled to the capsule 35 via the string-shaped member 50 (see FIG. 1), the capsule 35 is supported in the body via the string-shaped member 50 when the retaining portion is retained at the intended point 1a in the wall portion 1 in the body (see FIG. 6). At this time, since the capsule 35 is supported so as to hang down via the string-shaped member 50, the light from the light emitting member 30 is made less likely to be shielded, which allows the light to be irradiated on farther points.

It is to be noted that, in the treatment tool 10 in the present embodiment, the light emitting member 30 is placed on one end side in the axial direction of the power receiving coil 20 while the clip 40 defining the retaining portion is placed on the other side. Thus, as shown in FIG. 6, when the capsule 35 is retained at the intended point 1a in the wall portion 1 in the body via the clip 40 while the intended point 1a is, when a treatment subject lies on his/her back, located on the upper side in the wall portion 1 in the body, the capsule 35 hangs down such that the light emitting member 30 is oriented downward via the string-shaped member 50, whereby light can be irradiated from a closer position on the affected area C generated in the wall portion 1 that is on the lower side when the treatment subject lies on his/her back.

In addition, when the treatment tool 10A shown in FIG. 7(a) is suspended to be supported at the intended point 1a on the upper side of the wall portion 1 in the body via the clip 40, the light emitting members 30, 30 can be brought close to the affected areas C, C generated on the upper and lower sides of the wall portion 1 in the body as shown in FIG. 6, whereby the light can be irradiated on the affected areas C, C in an efficient manner. It is to be noted that when the treatment tool 10B shown in FIG. 7(b) is suspended to be supported at an intended point on the upper side of the wall portion 1 in the body via the clip 40, the light emitting member 30 can be brought close to an affected area C generated on a lateral side in the circumferential direction of the wall portion 1 in the body, whereby the light can be irradiated on the affected area C in an efficient manner.

In addition, in the present embodiment, the power receiving coil 20 is connected to the light emitting member 30 that defines the light-emitting diode via the resonance capacitor 31 arranged in parallel to the power receiving coil 20 as shown in FIG. 1 and FIG. 2(b). Thus, the simple circuit including the power receiving coil 20 and the resonance capacitor 31 allows the light-emitting diode that defines the light emitting member 30 to emit light, which can reduce the size of the capsule 35 housing these components.

Further, in the present embodiment, the transmission antenna 70 is made of the conductive wire 71 wound into a planar spiral shape as shown in FIG. 2(b). Therefore, supplying the transmission antenna 70 with alternating power can generate an intense magnetic field, and whatever posture the treatment tool 10 or the treatment tool 10A adopts, the transmission antenna 70 can be shifted in the X-direction and/or Y-direction with the use of unillustrated shifting means as shown in FIG. 5 to change the relative position between the transmission antenna 70 and the treatment tools 10, 10A, whereby the direction of the magnetic field diverged by the transmission antenna 70 is made to coincide with the cylinder axial directions of the power receiving coils 20 housed in the treatment tools 10, 10A, which can increase the power generation efficiency, and thus the light emitting member 30 can emit light with enough intensity.

Figure 9:
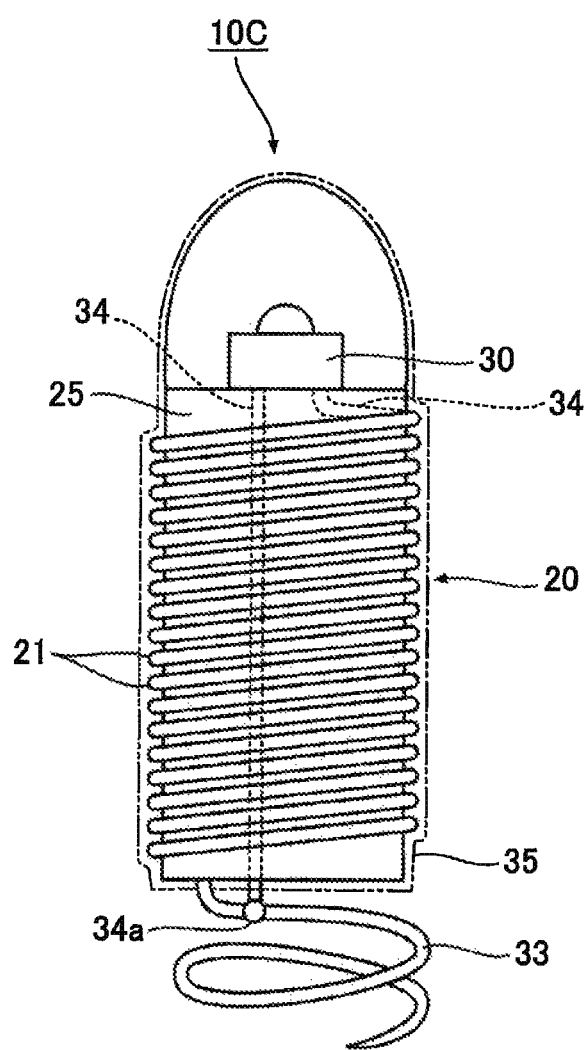
FIG. 9 is an explanatory view of a light emitting type capsule treatment tool according to the present invention in the second embodiment.

FIG. 9 shows a light emitting type capsule treatment tool according to the present invention in the second embodiment. It is to be noted that the same reference numerals are provided to the components that are substantially same as those in the above-described embodiment, and explanations of those components are omitted.

A light emitting type capsule treatment tool 10C in the present embodiment (hereinafter, referred to as the "treatment tool 10C") has a retaining portion different in structure from the one in the above-described embodiment. To be specific, the retaining portion of the treatment tool 10C in the present embodiment defines a puncture portion 33 that is a portion of the conductive wire 21 wound around the power receiving coil 20, the portion extending from an end portion of the power receiving coil 20 (here, the end portion on the other end side in the axial direction of the power receiving coil 20 that is opposite to the side where the light emitting member 30 is) and formed into a shape capable of sticking into tissue in a body. In addition, the light emitting member 30 includes a pair of lead wires 34, 34, one of which is connected to one end side in the axial direction of the power receiving coil 20 while the other one is drawn from the interior space of the power receiving coil 20 to the other end side in the axial direction of the power receiving coil 20, and is connected to the base end side of the puncture portion 33 via a silver solder 34a. It is to be noted that the above-described puncture portion 33 protrudes from the outer circumference of the capsule 35.

According to the treatment tool 10C in the present embodiment, since the retaining portion defines the puncture portion 33 that is a portion of the conductive wire 21 wound around the power receiving coil 20, the portion extending from the end portion of the power receiving coil 20 and formed into a shape capable of sticking into tissue in a body, the power receiving coil 20 and the retaining portion are of a monolithic construction, which can achieve a simple configuration and also bring down the cost of manufacturing.

Figure 10:
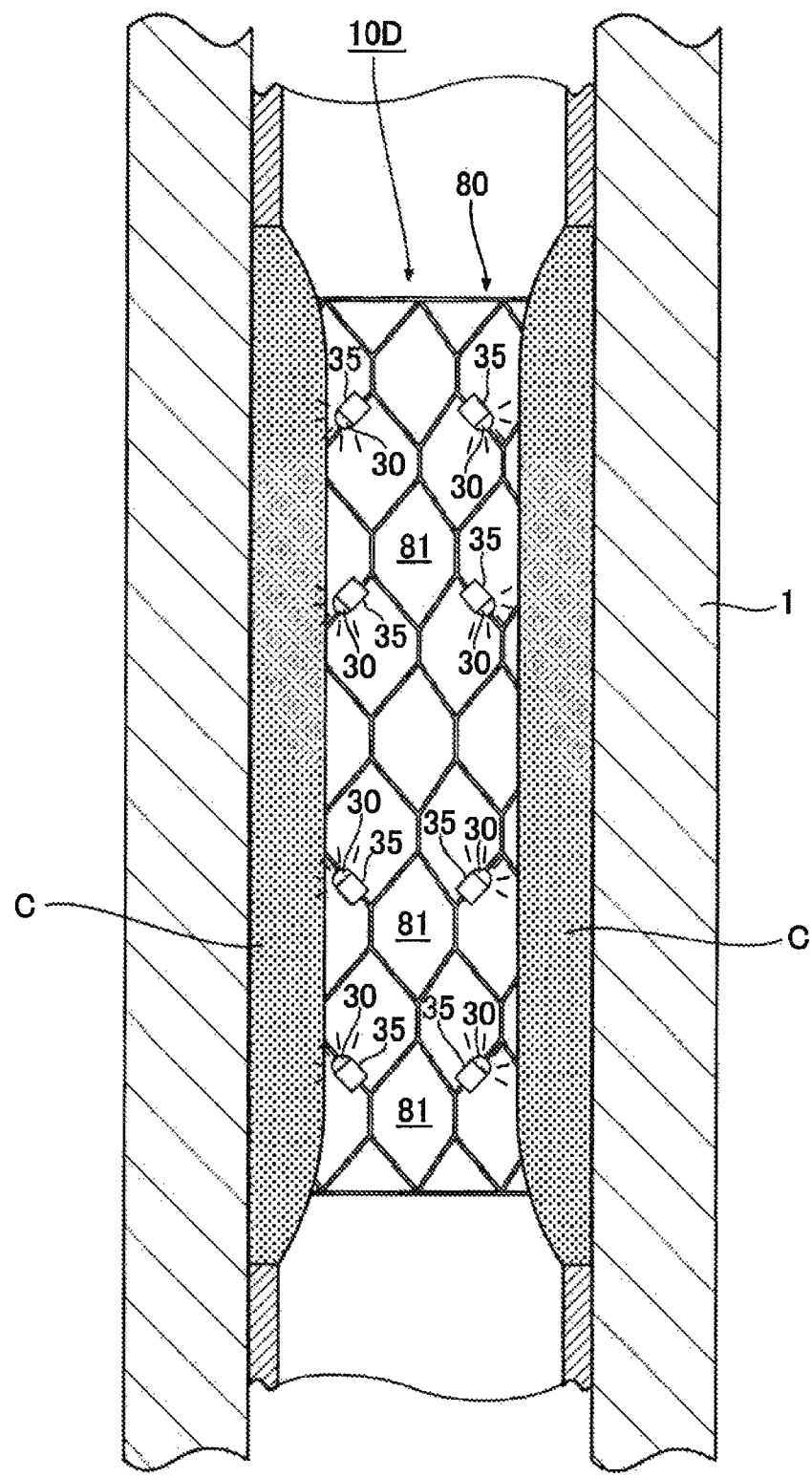
FIG. 10 is an explanatory view of a light emitting type capsule treatment tool according to the present invention in the third embodiment.
Figure 11:
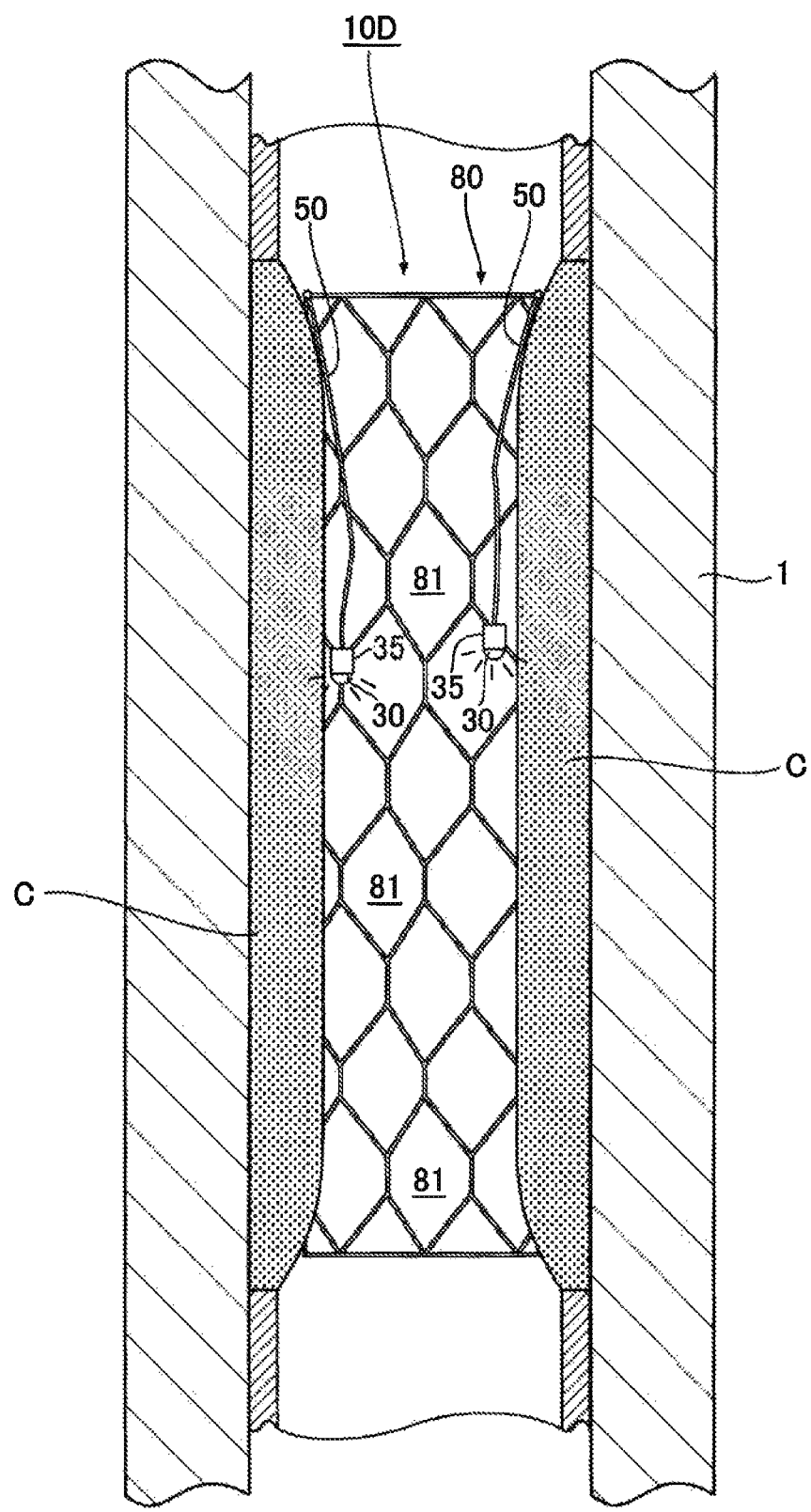
FIG. 11 is an explanatory view of a variant of the treatment tool in the third embodiment.

FIG. 10 and FIG. 11 show a light emitting type capsule treatment tool according to the present invention in the third embodiment. It is to be noted that the same reference numerals are provided to the components that are substantially same as those in the above-described embodiment, and explanations of those components are omitted.

A light emitting type capsule treatment tool 10D in the present embodiment (hereinafter, referred to as the "treatment tool 10D") has a retaining portion that defines a stent 80 configured to be retained on an inner circumference of the wall portion 1 in a body and including a mesh opening 81. The capsules 35 are coupled to the stent 80 directly (see FIG. 10) or via the string-shaped bodies 50 (see FIG. 11).

In the case of the treatment tool 10D shown in FIG. 10, a plurality of capsules 35 placed in the circumferential direction of the stent 80 are arranged in rows in the axial direction. Meanwhile, in the case of the treatment tool 10D shown in FIG. 11, a plurality of capsules 35 are coupled to one end side in the axial direction of the stent 80 via the string-shaped bodies 50 such that the plurality of capsules 35 may, when the one end side in the axial direction of the stent 80 is in the upward direction, hang down via the string-shaped bodies 50 to be placed at some midpoint in the axial direction of the stent 80.

It is to be noted that the stent 80 may be a stent made of a metal cylinder including a mesh opening 81 formed by laser processing, etching, or the like, or a stent made by weaving, braiding, or twisting metal wires into a cylinder including a mesh opening 81, and is not particularly limited.

According to the treatment tool 10D in the present embodiment, since the retaining portion defines the stent 80 including the mesh opening 81, the treatment tool 10D can be indwelled at predetermined points in a body with the use of a stent indwelled in tubular organs such as a biliary duct and a pancreatic duct.

Figure 12:
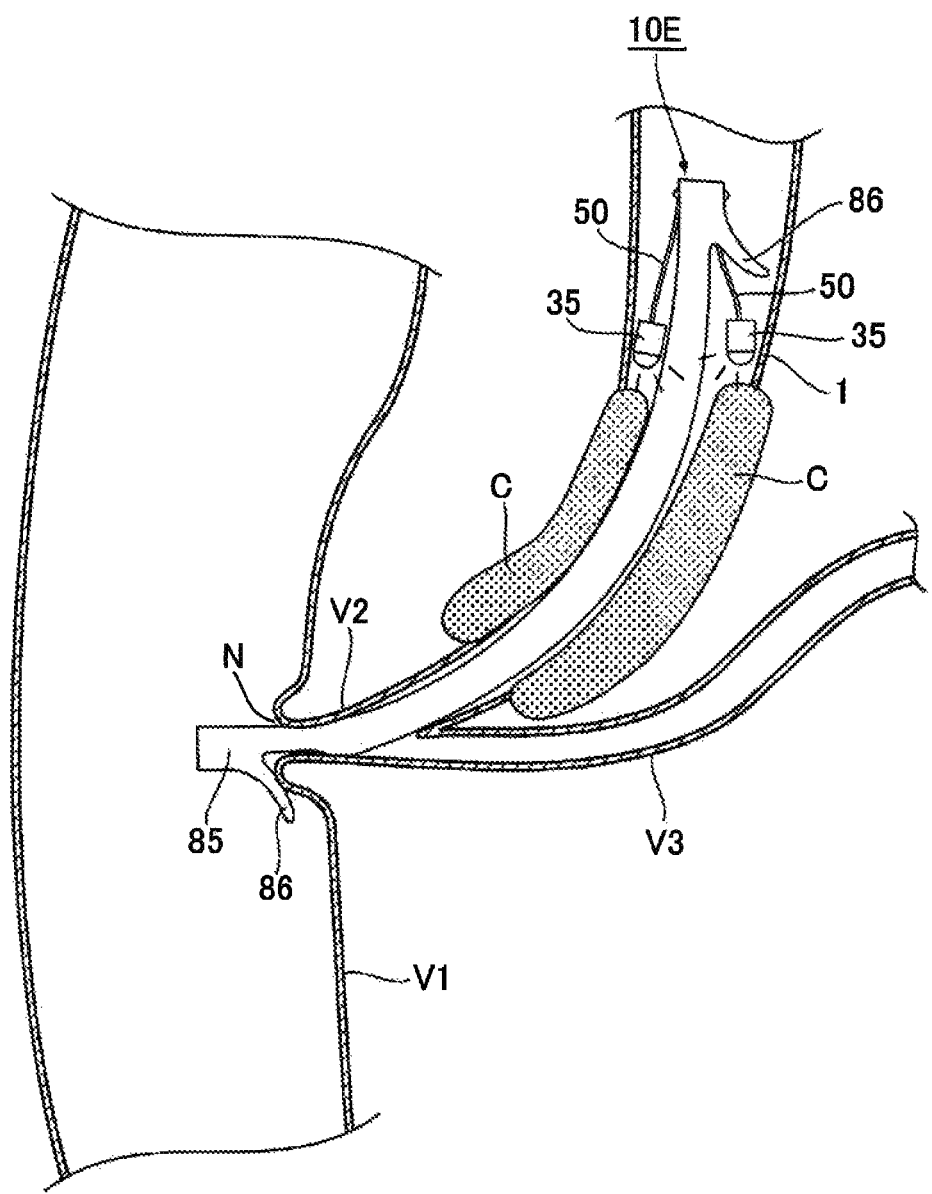
FIG. 12 is an explanatory view of a light emitting type capsule treatment tool according the present invention in the fourth embodiment.

FIG. 12 shows a light emitting type capsule treatment tool according to the present invention in the fourth embodiment. It is to be noted that the same reference numerals are provided to the components that are substantially same as those in the above-described embodiment, and explanations of those components are omitted.

A light emitting type capsule treatment tool 10E in the present embodiment (hereinafter, referred to as the "treatment tool 10E") has a retaining portion that defines a tube stent 85 including engaging portion for engaging the tube stent 85 with the inner circumference of the wall portion 1 in a body. The tube stent 85 has a tube shape with both ends opened including a path inside, and includes flaps 86, 86 at the both ends in the axial direction of the tube stent 85.

Each flap 86 has its one end coupled to the tube stent 85 and the other end having a free end shape bending to protrude outward, and the flaps 86 function as the engaging portion for engaging the tube stent 85 with the inner circumference of the wall portion 1 of a tubular organ such as a biliary duct V2 and other tissue. In addition, the capsules 35 are coupled to one end side of the tube stent 85 (the end portion of the tube stent 85 that is located on the deeper side in the inserting direction into a body) via the string-shaped bodies 50. It is to be noted that the capsules 35 may be coupled directly to the tube stent 85.

The tube stent 85 can be indwelled, for example, in the biliary duct V2 as shown in FIG. 12. The biliary duct V2 extends from the papilla N provided at a lower portion of the intestine duodenum V1, and also a pancreatic duct V3 branches off to extend from the papilla N.

The tube stent 85 is inserted, for example, via an unillustrated endoscope, and the one end side of the tube stent 85 is placed deeper in the biliary duct V2, and the flap 86 that defines the engaging portion is retained at the vicinity of the entrance of the papilla N, whereby the tube stent 85 can be indwelled in the biliary duct V2. At this time, since the capsules 35 are coupled to the one end side of the tube stent via the string-shaped bodies 50, light with a specific wavelength can be irradiated on affected areas C from the depth in an efficient manner.

As described above, by indwelling the treatment tool 10E in the present embodiment, for example, in tubular organs such as the biliary duct V2 and the pancreatic duct V3, not only the treatment tool 10E can be indwelled with the use of the stent 85, but also the treatment tool 10E can secure a path inside of the tube stent 85.

Figure 13:
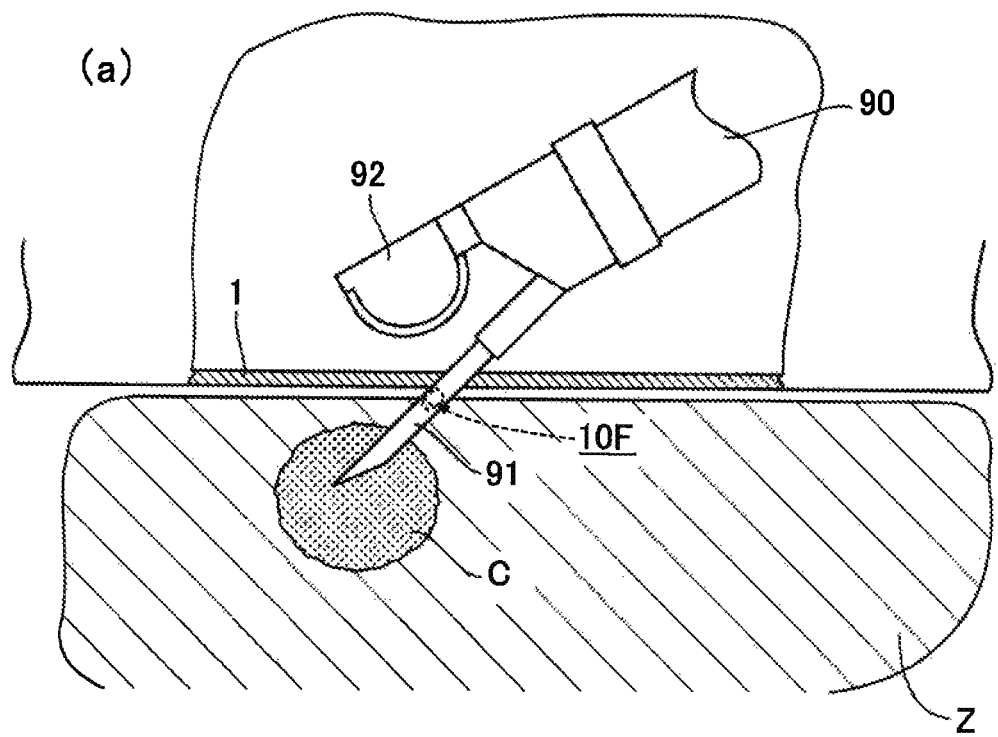
FIG. 13 are views of a light emitting type capsule treatment tool according to the present invention in the fifth embodiment, where
Figure 13:
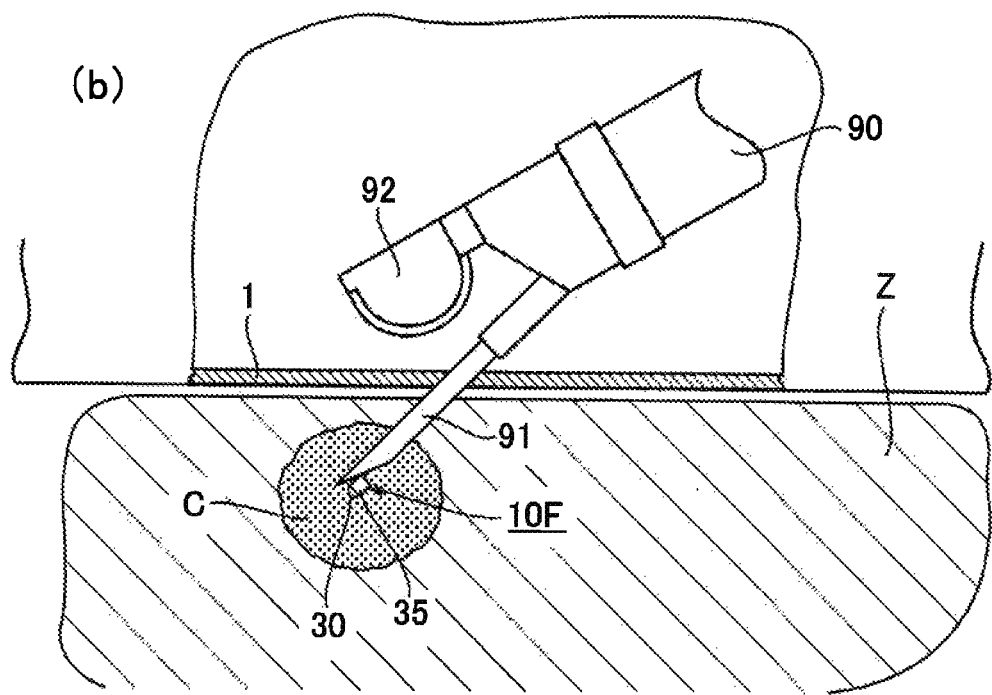

FIG. 13 shows a light emitting type capsule treatment tool according to the present invention in the fifth embodiment. It is to be noted that the same reference numerals are provided to the components that are substantially same as those in the above-described embodiment, and explanations of those components are omitted.

A light emitting type capsule treatment tool 10F in the present embodiment (hereinafter, referred to as the "treatment tool 10F") has a capsule 35 (see FIG. 13(b)) having a size and a shape capable of passing through the inside of the needle of the biopsy needle 91. In the case of the treatment tool 10F in the present embodiment, the treatment tool 10F is to be used in the biopsy needle 91 protruding from the tip opening of an ultrasonic endoscope 90 as shown in FIG. 13(a); however, the use of the treatment tool 10F is not limited only to the use in a biopsy needle for an ultrasonic endoscope. It is to be noted that an ultrasonic probe (probe) 92 for ultrasonic irradiation and detection is provided to the distal end of the ultrasonic endoscope 90.

In indwelling the treatment tool 10F, for example, in an affected area C in an organ Z such as a pancreas adjacent to a wall portion 1 of a stomach, the following procedure is carried out. That is, the ultrasonic endoscope 90 is inserted from the mouth, the distal end portion of the ultrasonic endoscope 90 is placed inside of the stomach, ultrasonic waves are irradiated from the inner surface side of the wall portion 1 of the stomach with the use of the ultrasonic probe 92, and the intended affected area C in the adjacent organ Z such as a pancreas where the treatment tool 10F is to be indwelled is detected. Then, as shown in FIG. 13(a), the biopsy needle 91 is projected from the tip opening of the ultrasonic endoscope 90 to penetrate the wall portion 1 of the stomach, and the biopsy needle 91 punctures the affected area C in the organ Z such as a pancreas. Then, further, the treatment tool 10F is indwelled in the affected area C through the inside of the needle of the biopsy needle 91 with the use of an unillustrated tube, sheath, pusher, or the like.

As described above, in the present embodiment, since the capsule 35 has a size and a shape capable of passing through the inside of the needle of the biopsy needle 91, the capsule 35 can be implanted inside the affected area C, for example, by protruding the needle of the biopsy needle 91 from the tip opening of the ultrasonic endoscope, and inserting the needle into the affected area C requiring treatment in the organ Z, and then making the capsule 35 pass through the needle of the biopsy needle 91. As a result of that, the capsule 35 can be indwelled so as to be imbedded in the affected area C to be treated in the organ Z such as a pancreas, and thus the treatment tool 10F can be indwelled appropriately even in the affected area C in the organ Z such as a pancreas where the treatment tool cannot be easily indwelled with the above-described clip 40 or the stent 80 (the effect of claim 8). It is to be noted that, the organ Z where the treatment tool 10F in the present embodiment is to be indwelled may be any other organ than a pancreas, and is not particularly limited.

Figure 14:
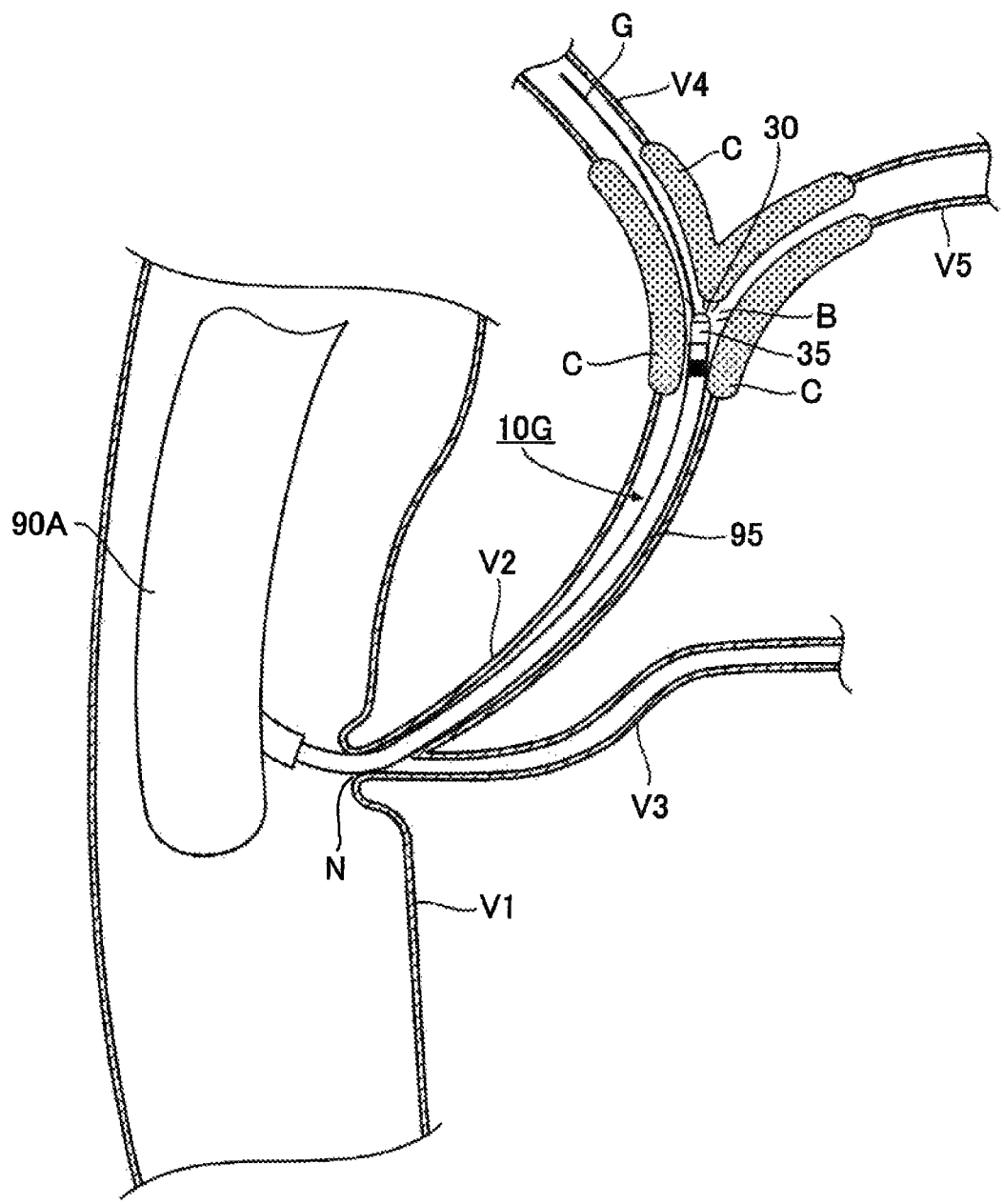
FIG. 14 is an explanatory view of a light emitting type capsule treatment tool according to the present invention in the sixth embodiment.

FIG. 14 shows a light emitting type capsule treatment tool according to the present invention in the sixth embodiment. It is to be noted that the same reference numerals are provided to the components that are substantially same as those in the above-described embodiment, and explanations of those components are omitted.

A light emitting type capsule treatment tool 10G in the present embodiment (hereinafter, referred to as the "treatment tool 10G") has a retaining portion defining a medical tube 95 configured to exit from a tip opening of an endoscope 90A and be inserted and indwelled at a predetermined position in a tubular organ. The capsule 35 is coupled directly to the distal end side of the medical tube 95. It is to be noted that the capsule 35 may be coupled to the distal end side of the medical tube 95 via the string-shaped member 50.

The light emitting type capsule treatment tool 10G in the present embodiment is preferably used to irradiate light, for example, on affected areas C generated in a wall portion 1 around a branching portion B including branching tubes V4, V5 branching off to extend from the deeper side of a biliary duct V2.

To be specific, after the endoscope 90A is indwelled in an intestine duodenum V1, the medical tube 95 exits from the tip opening of the endoscope 90A to be inserted, via a guide wire G, into the biliary duct V2 through a papilla N, and the distal end portion of the medical tube 95 is placed at the branching portion B, whereby the capsule 35 is placed. While this state is being kept, light from the light emitting member 30 can be irradiated on the affected areas C generated in the wall portion 1 around the branching portion B.

In the present embodiment, since the retaining portion defines the medical tube 95 configured to exit from the tip opening of the endoscope 90A and be inserted and indwelled at a predetermined position in a tubular organ, it is possible to indwell, while observation is carried out with the use of the endoscope 90A, the treatment tool 10G at such a point that the treatment tool l0F cannot be easily indwelled such as the branching portion B in the tubular organ including the biliary duct V2 and the pancreatic duct V3, whereby light can be irradiated in an effective manner on a point where light cannot be easily irradiated.

Figure 15:
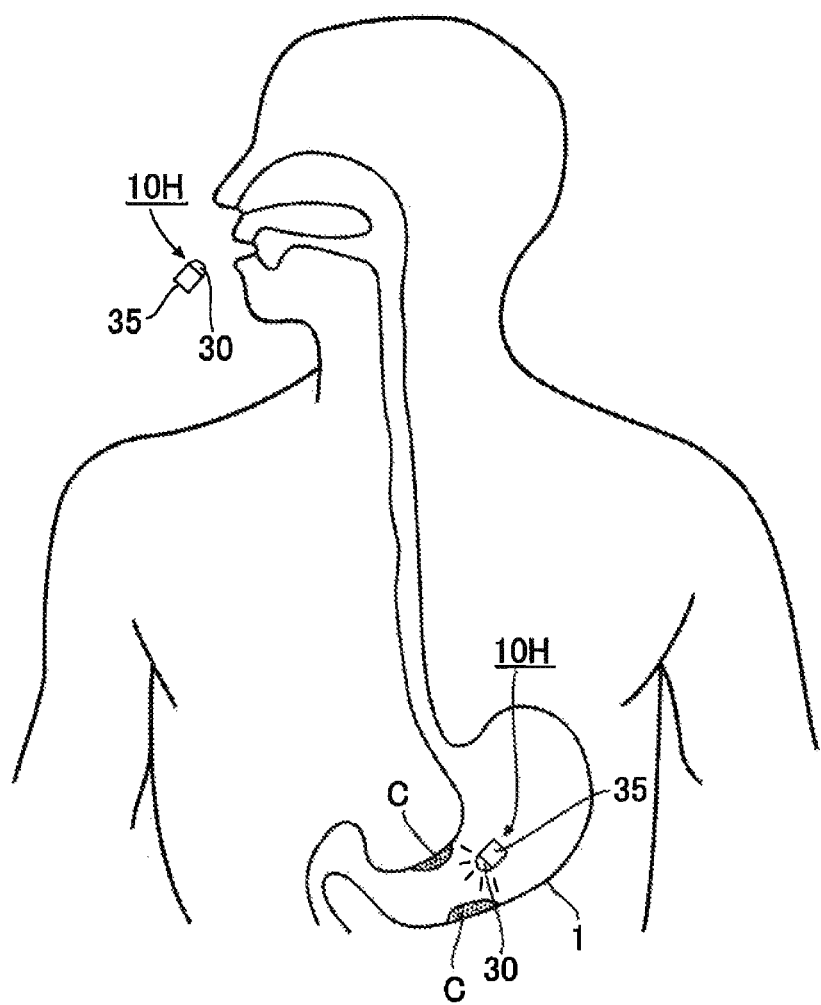
FIG. 15 is an explanatory view of a light emitting type capsule treatment tool according to the present invention in the seventh embodiment.

FIG. 15 shows a light emitting type capsule treatment tool according to the present invention in the seventh embodiment. It is to be noted that the same reference numerals are provided to the components that are substantially same as those in the above-described embodiment, and explanations of those components are omitted.

A light emitting type capsule treatment tool 10H in the present embodiment (hereinafter, referred to as the "treatment tool 10H") has a configuration including no retaining portion. However, the treatment tool 10H is provided with means with which the position of the treatment tool 10H can be recognized from the outside, for example, the treatment tool 10H may be provided with an unillustrated built-in camera, or may have a capsule 35 a part of which is provided with an X-ray impermeable marker.

As shown in FIG. 15, the capsule 35 is swallowed from the mouth, and the treatment tool 10H is identified in advance with the use of images taken by the camera or X-ray images, and then when the treatment tool 10H arrives in the vicinity of the affected areas C in the wall portion 1 in the body, light can be irradiated from the light emitting member 30 via the transmission antenna 70.

It is to be noted that the present invention is not limited to the embodiments described above, but various modified embodiments may be made without departing from the scope of the present invention, and those modified embodiments can also be included within the scope of the present invention.

REFERENCE SIGNS LIST

10, 10A, 10B, 10C, 10D, 10E, 10F, 10G, 10H
Light emitting type capsule treatment tool (Treatment tool)
20 Power receiving coil
21 Conductive wire
25 Magnetic member
30 Light emitting member
31 Resonance capacitor
35 Capsule
40 Clip
41 Holding piece
45 Slider
50 String-shaped member
60 Carrier device
70 Transmission antenna
80 Stent
81 Opening
85 Tube stent
90 Ultrasonic endoscope
90A Endoscope
91 Biopsy needle
95 Medical tube

The invention claimed is:

1. A light emitting type capsule treatment tool for irradiating light with a specific wavelength required for photoimmunotherapy, comprising:
   a power receiving coil formed by winding a conductive wire and configured to receive electric power supplied from an external transmission antenna via a magnetic flux;
   a magnetic member placed on an inner circumference of the power receiving coil;
   a light emitting member configured to be supplied with electric power from the power receiving coil and to emit the light with the specific wavelength;
   a capsule housing the power receiving coil, the magnetic member and the light emitting member; and
   a retaining portion configured to retain the capsule at an intended point in a body,
   wherein the retaining portion includes a portion of the conductive wire, the portion extending from an end portion of the power receiving coil and formed into a shape capable of sticking into tissue in a body.

2. The light emitting type capsule treatment tool according to claim 1, wherein
the power receiving coil is connected to a light-emitting diode performing as the light emitting member via a resonance capacitor arranged in parallel thereto.

3. The light emitting type capsule treatment tool according to claim 1, wherein
the transmission antenna includes a conductive wire wound into a planar spiral shape.

* * * * *